United States Patent [19]

Wollweber et al.

[11] Patent Number: 4,904,687
[45] Date of Patent: Feb. 27, 1990

[54] FUNGICIDAL SUBSTITUTED 3-ARYLPYRROLES

[75] Inventors: Detlef Wollweber, Wuppertal; Wilhelm Brandes, Leichlingen, both of Fed. Rep. of Germany

[73] Assignee: Bayer Aktiengesellschaft, Leverkusen, Fed. Rep. of Germany

[21] Appl. No.: 220,055

[22] Filed: Jul. 15, 1988

[30] Foreign Application Priority Data

Jul. 24, 1987 [DE] Fed. Rep. of Germany ....... 3724554

[51] Int. Cl.$^4$ .................. C07D 401/04; C07D 409/04; C07D 407/04; C07D 207/34
[52] U.S. Cl. .................................... 514/427; 514/343; 514/422; 546/281; 548/517; 548/526; 548/527; 548/561
[58] Field of Search ............... 548/526, 561, 517, 527; 514/422, 427, 343; 546/281

[56] References Cited

U.S. PATENT DOCUMENTS 4,716,237 12/1987 Drauz .................................. 548/561

FOREIGN PATENT DOCUMENTS 0174910 3/1986 European Pat. Off. .
0182738 5/1986 European Pat. Off. .

*Primary Examiner*—Mark L. Berch
*Attorney, Agent, or Firm*—Sprung Horn Kramer & Woods

[57] ABSTRACT

Fungicidally active substituted 3-arylpyrroles of the formula

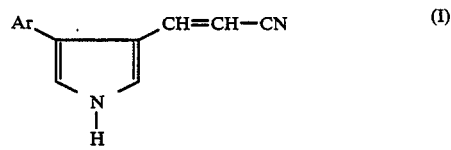

in which
Ar represents optionally substituted aryl or optionally substituted heteroaryl.

9 Claims, No Drawings

FUNGICIDAL SUBSTITUTED 3-ARYLPYRROLES

The invention relates to new substituted 3-arylpyrroles, a process for their preparation and their use as pest combating agents.

It has already been disclosed that certain substituted 3-arylpyrroles, such as, for example, 3-(2,3-dichlorophenyl)-4-cyano-pyrrole, possess fungicidal properties (compare EP 174,910 and EP 182,738).

However, the activity of these previously known compounds is not completely satisfactory in all fields of application, in particular at low application rates and concentrations. The tolerance for plants is also occasionally problematic in representatives of this class of substances.

New substituted 3-arylpyrroles of the general formula (I)

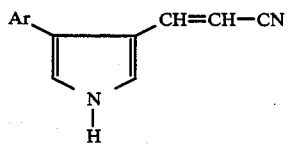

in which

Ar represents optionally substituted aryl or optionally substituted heteroaryl, have been found.

The compounds of the formula (I) can exist as geometric isomers or isomeric mixtures of varying composition. The pure isomers and the isomeric mixtures are claimed according to the invention.

It has furthermore been found that the new substituted 3-arylpyrroles of the general formula (I)

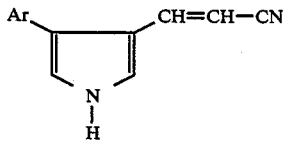

in which

Ar represents optionally substituted aryl or optionally substituted heteroaryl, are obtained when 3-aryl-pyrrole-4-aldehydes of the formula (II)

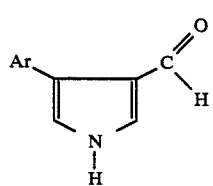

in which

Ar has the abovementioned meaning, are reacted either (a) with triphenylphosphonium salts of the formula (III)

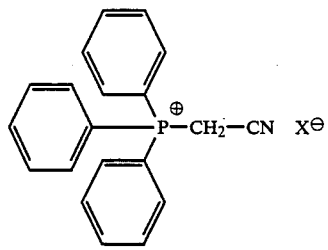

in which $X^\ominus$ represents a suitable counter-ion, or (b) with a phosphonate of the formula (IV)

in which

R represents alkyl, if appropriate in the presence of a base and in the presence of a diluent.

Finally, it has been found that the new substituted 3-arylpyrroles of the general formula (I) possess a good action against pests.

Surprisingly, the substituted 3-aryl-pyrroles of the general formula (I), according to the invention, show a better activity against fungal plant pests than the substituted 3-arylpyrroles known from the prior art, such as, for example, 3-(2,3-dichlorophenyl)-4-cyano-pyrrole, which are related compounds chemically and with respect to their action and, moreover, they exhibit a considerably better tolerance for plants.

Formula (I) provides a general definition of the substituted 3-arylpyrroles according to the invention. Preferred compounds of the formula (I) are those in which Ar represents pyridyl, furyl or thienyl which is in each case optionally monosubstituted to polysubstituted by identical or different substituents from the series comprising halogen, nitro and straightchain or branched alkyl having 1 to 4 carbon atoms, or phenyl which is optionally monosubstituted to polysubstituted by identical or different substituents, suitable substituents being: halogen, cyano, nitro, in each case straightchain or branched alkyl, alkoxy, alkylthio or alkoxycarbonyl having in each case 1 to 6 carbon atoms, in each case straight-chain or branched halogenoalkyl, halogenoalkoxy or halogenoalkylthio having in each case 1 to 4 carbon atoms and 1 to 9 identical or different halogen atoms, phenyl and also divalent, optionally fluorine-substituted dioxyalkylene having 1 or 2 carbon atoms. Particularly preferred compounds of the formula (I) are those in which Ar represents 2-pyridyl, 3-pyridyl, 4-pyridyl, 3-furyl, 2-furyl, 3-thienyl or 2-thienyl which is in each case optionally monosubstituted, disubstituted or trisubstituted by identical or different substituents from the series comprising fluorine, chlorine, bromine, methyl and ethyl, or phenyl which is optionally monosubstituted, disubstituted or trisubstituted by identical or different substituents, suitable substituents being: fluorine, chlorine, bromine, methyl, ethyl, n- or i-propyl, methoxy, ethoxy, methylthio, trifluorometyl, trifluoromethoxy, trifluoromethylthio, cyano, notro, phenyl, dioxymetholene and dixydifluoromethylene. Very particularly preferred compounds of the formula (I) are those in which Ar represents phenyl which is optionally monosubstituted or disubstituted by identical or different substituents, suitable substituents being: fluorine, chlorine, bromine, methyl, ethyl, methoxy, ethoxy, methylthio, trifluoromethyl, trifluoromethoxy, trifluoromethylthio, nitro and dioxydifluoromethylene; or 2-pyridyl, 4-pyridyl, 2-furyl or 2-thienyl which is in each case optionally nonosubstituted or disubstituted by chlorine and/ or methyl.

The following substituted 3-arylpyrroles of the general formula (I)

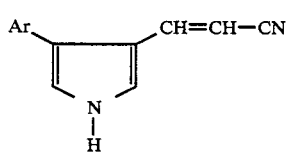

may be individually mentioned in addition to the compounds mentioned in the preparation examples:

If, for example, 3-(2-chlorophenyl)-pyrrole-4-aldehyde and triphenylcyanomethylphosphonium chloride are used as starting materials, then the course of the reaction of the process (a) according to the invention can be represented by the following equation:

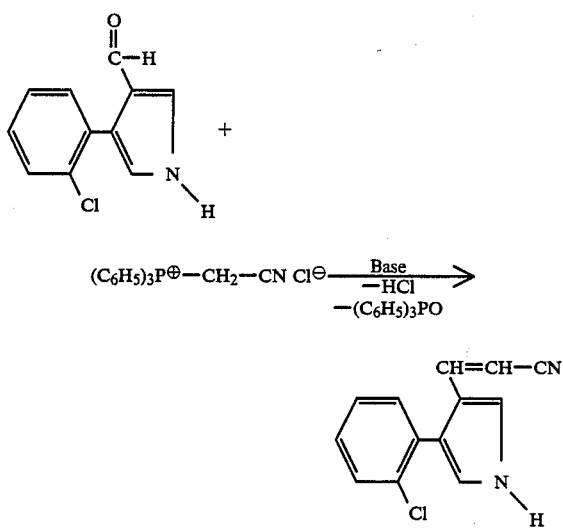

If, for example, 3-(2-methylphenyl)-pyrrole-4-aldehyde and diethyl cyanomethylphosphonate are used as starting materials, then the course of the reaction of the process (b) according to the invention can be represented by the following equation:

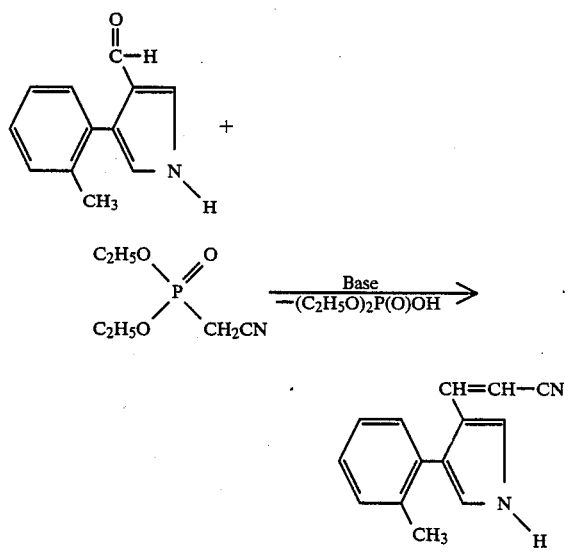

Formula (II) provides a general definition of the 3-arylpyrrole-4-aldehydes required as starting materials for carrying out the processes (a) and (b) according to the invention. In this formula (II), Ar preferably represents those radicals which have already been mentioned as preferred for this substituent in connection with the description of the substances of the formula (I) according to the invention.

The 3-aryl-pyrrole-4-aldehydes of the formula (II) are known (compare, for example, EP 174,910) or are obtainable analogously to known processes, for example when 4-cyano-3-aryl-pyrroles of the formula (V)

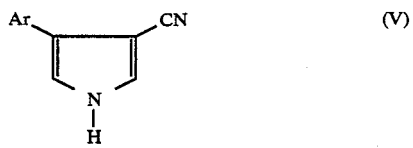

in which

Ar has the abovementioned meaning, are reacted with reductants such as, for example, diisobutylaluminum hydride, if appropriate in the presence of a diluent such as, for example, toluene, at temperatures between −20° C. and +80° C.

The 4-cyano-3-aryl-pyrroles of the formula (V) are known (compare, for example, EP 174,910 or EP 182,738).

Formula (III) provides a general definition of the triphenylphosphonium salts required as starting materials for carrying out the process (a) according to the invention. In this formula (III), X preferably represents halogen, in particular chlorine or bromine.

The triphenylphosphonium salts of the formula (III) are generally known compounds of organic chemistry.

Formula (IV) provides a general definition of the phosphonate required as starting materials for carrying out the process (b) according to the invention. In this formula (IV), R preferably represents straight-chain or branchedalkyl having 1 to 4 carbon atoms, in particular methyl or ethyl.

The phosphonates of the formula (IV) are likewise generally known compounds of organic chemistry.

Suitable diluents for carrying out the processes (a) and (b) according to the invention are inert organic solvents. In particular, these include aliphatic, alicyclic or aromatic, optionally halogenated hydrocarbons such as, for example, benzine, benzene, toluene, xylene, chlorobenzene, petroleum ether, hexane, cyclohexane, dichloromethane, chloroform or carbon tetrachloride, ethers, such as diethyl ether, dioxane, tetrahydrofuran or ethylene glycol dimethyl or diethyl ether, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, or sulphoxides, such as dimethyl sulphoxide.

The processes (a) and (b) according to the invention are preferably carried out in the presence of a suitable base. Those which are suitable are all customarily utilizable aprotic, inorganic and organic bases. Hydrides, amides or alcoholates of alkali metals such as, for example, sodium hydride, sodium amide, sodium-methylate, sodium ethylate, potassium t-butylate and also organometallic compounds such as, for example, n-butyllithium are preferably used.

The reaction temperatures can be varied within a relatively wide range when carrying out the processes (a) and (b) according to the invention. In general, the reaction is carried out at temperatures between −20° C. and +120° C., preferably at temperatures between 0° and 80° C.

When carrying out process (a) according to the invention, 1.0 to 3.0 mols, preferably 1.0 to 2.0 mols, of triphenylphosphonium salt of the formula (III) and 1.0 to 3.0 mols, preferably 1.0 to 2.0 mols, of base are employed per mol of 3-aryl-pyrrole-4-aldehyde of the formula (II).

The reaction is carried out and the reaction products are worked up and isolated by generally customary methods (compare, for example, "Organikum"; 15th edition, p. 494; VEB Deutscher Verlag der Wissenschaften, Berlin 1981, and also the preparation examples).

When carrying out the process (b) according to the invention, 1.0 to 3.0 mols, preferably 1.0 to 2.0 mols, of phosphonate of the formula (IV) and if appropriate 1.0 to 3.5 mol s, preferably 1.0 to 2.5 mols, of base are employed per mol of 3-aryl-pyrrole-4-aldehyde of the formula (II).

In a preferred embodiment, it is possible to prepare the phosphonate of the formula (IV), employed as the starting compound, from trialkyl phosphite and halogenoacetonitrile in an initial reaction and to further react it directly from the reaction mixture by the pr9cess (b) according to the invention.

The reaction is carried out and the reaction products are worked up and isolated by generally customary methods (compare, for example, Synthesis 1969, 170 or Synthesis 1977, 126, and also the preparation examples).

The compounds according to the invention exhibit a strong action against pests and can be practically employed for combating undesired harmful organisms. The active compounds are used in particular as fungicides for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation: Pythium species, such as, for example, Pythium ultimum; Phytophthora species, such as, for example, *Phytophthora infestans;* Pseudoperonospora species, such as, for example, *Pseudope-ronospora h-umuli* or *Pseudoperonospora cubensis;* Plasmopara species, such as, for example, Plasmopara viticola; Peronospora species, such as, for example, Peronospora pisi or P. brassicae; Erysiphe species, such as, for example, *Erysiphe graminis;* Sphaerotheca species, such as, for example, Sphaerotheca fuliginea; Podosphaera species, such as, for example, *Podosphaera leucotricha;* Venturia species, such as, for example, Venturia inaequalis; Pyrenophora species, such as, for example, Pyrenophora teres or P. graminea (conidia form: Drechslera, syn: Helminthosporium); Cochliobolus species, such as, for example, *Cochliobolus sativus* (conidia form: Drechslera, syn: Helminthosporium); Uromyces species, such as, for example, Uromyces appendiculatus; Puccinia species, such as, for example, *Puccinia recondita;* Tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, Pyricularia oryzae; Fusarium species, such as, for example, *Fusarium culmorum;* Botrytis species, such as, for example, *Botrytis cinerea;* Septoria species, such as, for example, *Septoria nodorum;* Leptosphaeria species, such as, for example, Leptosphaeria nodorum; Cercospora species, such as, for example, Cercospora canescens; Alternaria species, such as, for example, Alternaria brassicae; and Pseudocercosporella species, such as, for example, *Pseudocercosporella herpotrichoides.*

In this case, the compounds according to the invention can be used with particularly good effect for combating diseases in the production of fruit and vegetables such as, for example, against the causative organism of bean-grey mould (Botrytis cinerea) or for combating diseases of rice such as, for example, against the causativ organism of rice spot (Pyricularia oryzae).

In addition, the active compounds according to the invention show a good in vitro action in the mycelium growth test.

The active compounds can be converted to the customary formulations, such as solutions, emulsion, suspensions, powders, foams, pastes, granules, aerosols, very fine capsules in polymeric substances and in coating compositions for seed, as well as ULV formulations.

These formulations are produced in known manner, for example bymixing the active compounds with extenders, that is, liquid solvents, liquefied gases under pressure, and/or solid carriers, optionally with the use of surfaceactive agents, that is, emulsifying agents ad/or dispersing agents, and/or foam-formaing agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters ketones, such as acetone, methyl ethyl ketone, methyl isobutyl ketone or cyclonehexanone, strongly polar solvents, such as dimethylformamede and dimethyl sulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

EXAMPLE 1

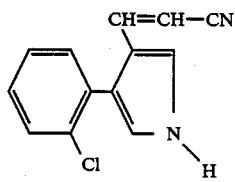

(Process a)

31.1 ml (0.0498 mol) of n-butyllithium in hexane (concentration 1.6 mol/l) are added dropwise at room temperature with stirring under a protective argon gas atmosphere to 16.8 g (0.0498 mol) of cyanomethyltriphenylphosphonium chloride in 30 ml of toluene, the mixture is then stirred for 1 hour after completion of the addition, 5.1 g (0.0249 mol) of 3-(2-chlorophenyl)-pyrrole-4-aldehyde in 120 ml of toluene/tetrahydrofuran mixture (1 : 3) are then added dropwise with stirring, the mixture is stirred for 12 hours at 50° C. after completion of the addition, then cooled to room temperature and filtered, the filtrate is diluted with ethyl acetate, washed using water and dried over sodium sulphate, and the solvent is removed in vacuo. The E/Z isomer mixture thus obtainable can be separated by chromatography on silica gel (eluant ethyl acetate/cyclohexane 1 : 5).

2.3 g (41% of theory) of (Z)-β-[3-(2-chlorophenyl)-pyrrol-4-yl]-acrylonitrile of melting point 145° C.-146° C. and 1.9 g (34% of theory) of (E)-β-[3-(2-chlorophenyl)pyrrol-4-yl]-acrylonitrile of melting point 142° C.-143° C. are obtained.

PREPARATION OF THE STARING COMPOUND

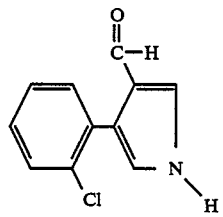

99 ml (0.1485 mol) of a 1.5 molar diisobutylaluminum hydride solution in toluene are added dropwise at −20° C. with stirring under a protective argon gas atmosphere to 15 g (0.0743 mol) of 3-(2-chlorophenyl)-pyrrole-4-carbonitrile in 300 ml of absolute toluene the mixture is stirred for 4 hours at −20° C. after completion of the addition, allowed to come to room temperature and hydrolyzed using 400 ml of 10% strength aqueous citric acid solution, the organic phase is separated off, the aqueous phase is washed with ether, the combined organic phases are dried over sodium sulphate and concentrated in vacuo, and the residue is chromatographed on silica gel (eluant ethyl acetate/cyclohexane 2 : 1).

11.8 g (78% of theory) of 3-(2-chlorophenyl)pyrrole-4-aldehyde of melting point 147° C.-148° C. are obtained.

EXAMPLE 2

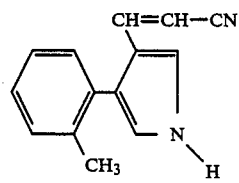

(Process b)

2.5 g (0.0326 mol) of chloroacetonitrile and 5.4 g (0.0326 mol) of triethyl phosphite are heated to 200° C. until the evolution of gas has ended. 30 ml of dimethylformamide and 1.8 g (0.034 mol) of sodium methylate are added to the cooled mixture and 3.0 g (0.0162 mol) of 3-(2-methylphenyl)-pyrrole-4-aldehyde in 5 ml of dimethylformamide are then added dropwise at 0° C. with stirring. After completion of the addition, the reaction mixture is stirred for 16 hours at room temperature and then added to water, the mixture is extracted with ethyl acetate, washed using water, dried over sodium sulphate and concentrated in vacuo, and the residue is purified by chromatography on silica gel (eluant ethyl acetate/cyclohexane 5 : 1). 0.5 g (15% of theory) of (Z)-β-[3-(2-methylphenyl)pyrrol -4-yl]-acrylonitrile of melting point 74° C.-75° C. and 1.2 g (36% of theory) of (E)-β-[3-(2-methylphenyl)pyrrol -4-yl]-acrylonitrile of melting point 152° C.-154° C. are obtained.

The following substituted 3-aryl-pyrroles of the general formula (I)

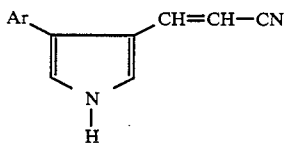

are obtained in a corresponding manner and according to the general instructions for preparation:

| Ex. No. | Ar | Melting point/°C. |
|---|---|---|
| 3 | Cl Cl (2,3-dichlorophenyl) | 153–154 (Z—form) |
| 4 | Cl Cl (2,3-dichlorophenyl) | 187–188 (E—form) |
| 5 | Cl CH₃ | 140–141 (Z—form) |
| 6 | Cl CH₃ | 152–154 (E—form) |
| 7 | Cl-phenyl | 154 |

Use examples

The compound shown below was employed as the comparison substance in the following use example:

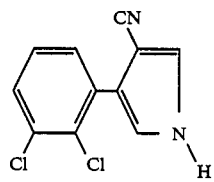

3-(2,3-Dichlorophenyl)-pyrrole-4-carbonitrile (known from EP 174,910)

EXAMPLE A

Botrytis test (bean)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar on which Botrytis cinerea has been grown are placed on each leaf. The inoculated plants are placed in a darkened humid chamber at 20° C. 3 days after the inoculation, the size of the infected spots on the leaves is evaluated.

In this test, for example, the compounds according to the preparation examples 1, 3 and 4 show a clear superiority in activity compared to the prior art.

It is understood that the specification and examples are illustrative but not limitative of the present invention and that other embodiments within the spirit and scope of the invention will suggest themselves to those skilled in the art.

We claim:

1. A substituted 3-arylpyrrole of the formula

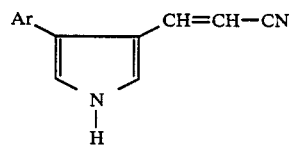

in which
Ar represents pyridyl, furyl or thienyl which is in each case optionally monosubstituted or polysubstituted by identical or different substituents from the group consisting of halogen, nitro and straight-chain or branched alkyl having 1 to 4 carbon atoms, or phenyl which is optionally monosubstituted or polysubstituted by identical or different substituents from the group consisting of halogen, cyano, nitro, straight-chain or branched alkyl, alkoxy, alkylthio or alkoxycarbonyl having in each case 1 to 6 carbon atoms, in each case straight-chain or branched halogenoalkyl, halogenoalkoxy or halogenoalkylthio having in each case 1 to 4 carbon atoms and 1 to 9 identical or different halogen atoms, phenyl and, optionally fluorine-substituted oxyalkyleneoxy having 1 to 2 carbon atoms.

2. A method of combating fungi which comprises applying to such fungi or to a fungus habitat a fungicidally effective amount of a compound according to claim 1.

3. A substituted 3-arylpyrrole according to claim 1, in which
Ar represents 2-pyridyl, 3-pyridyl, 4-pyridyl, 3-furyl, 2-furyl, 3-thienyl or 2-thienyl which is in each case optionally monosubstituted, disubstituted or trisubstituted by identical or different substituents from the group consisting of fluorine, chlorine, bromine, methyl and ethyl, or phenyl which is optionally monosubstituted, disubstituted or trisubstituted by identical or different substituents from the group consisting of fluorine, chlorine, bromine, methyl, ethyl, n- or i-propyl, methoxy, ethoxy, methylthio, trifluoromethyl, trifluoromethoxy, trifluoromethylthio, cyano, nitro, phenyl, dioxymethylene and dioxydifluoromethylene 4. A substituted 3-arylpyrrole according to claim 1, in which Ar represents phenyl which is optionally monosubstituted or disubstituted by identical or different substituents from the group consisting of fluorine, chlorine, bromine, methyl, ethyl, methoxy, ethoxy, methylthio, trifluoromethyl, trifluoromethoxy, trifluoromethylthio, nitro and dioxydifluoromethylene; or 2-pyridyl, 4-pyridyl, 2-furyl or 2-thienyl which is in each case optionally monosubstituted or disubstituted by chlorine and/or methyl.

5. A compound according to claim 1, wherein such compound is β-[3-(2-chlorophenyl)-pyrrol-4-yl]-acrylonitrile of the formula

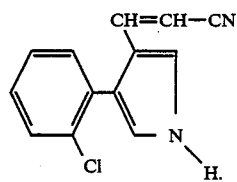

6. A compound according to claim 1, wherein such compound is β-[3-(2-methylphenyl)-pyrrol-4-yl]-acrylonitrile of the formula

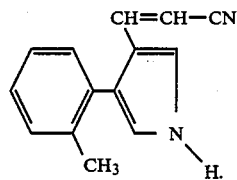

7. A compound according to claim 1, wherein such compound is β-[3-(2,3-dichlorophenyl)-pyrrol-4-yl]a-crylonitrile of the formula

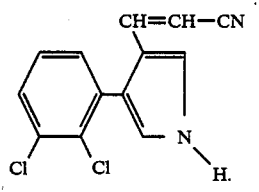

8. A fungicidal composition comprising a fungicidally effective amount of a compound according to claim 1 and a diluent.

9. The method according to claim 2, wherein such compound is
β-[3-(2-chlorophenyl)-pyrrol-4-yl]-acrylonitrile,
β-[3-(2-methylphenyl)-pyrrol-4-yl]-acrylonitrile and
β-[3-(2,3-dichlorophenyl)-pyrrol-4-yl]-acrylonitrile.

* * * * *